United States Patent [19]

Schäfer et al.

[11] Patent Number: 4,476,697
[45] Date of Patent: Oct. 16, 1984

[54] WOUND DRESSING

[75] Inventors: Ewald Schäfer, Wolfstein; Harald Jung, Kreimbach, both of Fed. Rep. of Germany

[73] Assignee: Karl Otto Braun KG

[21] Appl. No.: 498,452

[22] Filed: May 26, 1983

Related U.S. Application Data

[63] Continuation of Ser. No. 141,812, Apr. 21, 1980, Pat. No. 4,391,106, which is a continuation of Ser. No. 880,150, Feb. 22, 1978, abandoned.

[51] Int. Cl.³ .............................................. D04B 23/08
[52] U.S. Cl. ........................................ 66/193; 66/202; 128/156
[58] Field of Search .......................... 66/190, 195, 202; 128/156, 90, 82

[56] References Cited

U.S. PATENT DOCUMENTS 3,448,595  6/1969  Baltzer et al. ................... 66/193
3,570,482  3/1971  Emoto et al. .................... 66/193

*Primary Examiner*—Ronald Feldbaum
*Attorney, Agent, or Firm*—Toren, McGeady and Stanger

[57] ABSTRACT

The invention relates to a wound dressing which prevents or at least reduces sticking of the dressing to the surface of the wound due to contact with moisture from the wound and which without the use of over twisted threads has a controllable lifting action and an excellent secretion-absorbing action, whereby cutting of the dressing into strips does not lead to lateral fraying due to the cutting of the mesh as is the case with known knitted fabrics and in which the further use leads to complication. The present wound dressing comprises a knitted fabric formed with a basic stitch construction and with a plurality of inlay threads having a Z or S twist, the yarns of the inlay threads having the same thickness and twist, and being inserted as slightly or greatly displaced wefts.

5 Claims, 12 Drawing Figures

L1　　L2　　L3　　L4

L1　　L2　　L3　　L4

WOUND DRESSING

This is a continuation of application Ser. No. 141,812, filed Apr. 21, 1980, now U.S. Pat. No. 4,391,106, which is a continuation of application Ser. No. 880,1650, filed Feb. 22, 1978, now abandoned.

The present invention relates generally to warp knit fabrics and more particularly to such fabrics which are adapted for use as bandage materials.

It is known to use bandaging fabrics which prevent or at least reduce the sticking of the textile web to the surface of the wound when it is in contact with liquid from the wound particularly secretion, pus, blood and the like. In a known fabric there is shrinkage or swelling of the longitudinal threads or thread portions when liquid from the wound encounters the same leading to mutual movements which reduce or prevent the threads or thread portions sticking to one another and to the wound.

In order to achieve the same action as indicated hereinbefore a knitted fabric has been proposed in which a thick thread is tied in by a thin thread in the mesh layer, whereby the thick thread is highly twisted and runs in a linear or slightly displaced weft, being tied in by at least one very slightly twisted thread. The thick highly twisted thread is of size 34/2 and the very slightly twisted thread of size 40/1. In this known knitted fabric, the so-called "tunnel effect", i.e., the raising of the fabric from the wound so that it does not stick to the wound, is brought about through combining highly twisted threads, i.e. crepe threads, with lightly twisted monofilaments, the highly twisted threads having the S-twisting direction and the lightly twisted threads the Z-twisting direction. Depending on the square meter weight, it is possible to use a thread of size 34/1 instead of Nm 40/1 and a crepe thread of size Nm 40/2 instead of Nm 34/2. In a manner similar to that utilizing threads of size Nm 34/1, it is possible to use spun crepe threads, i.e., highly twisted monofilaments, e.g., of size Nm 20/1.

The aim of the present invention is to provide a wound dressing which prevents or at least reduces sticking of the web to the surface of the wound when in contact with moisture from the wound, particularly secretion, and which without the use of over twisted threads has a controllable lifting action and has a good absorptive action for secretion. Furthermore, when cut into strips, it does not, like the known knitted fabrices, become laterally frayed due to cutting of the mesh, leading to complications during subsequent use.

According to the invention, this problem is solved by a wound dressing which, according to the invention, is constructed in such a way that said dressing comprises a knitted fabric formed of a basic stitch construction and with a plurality of in-laid threads made from yarn having a Z- or S-twist, the yarns of the in-laid threads having the same thickness and twist and being inserted as slightly or greatly displaced wefts.

More specifically, the in-laid comprise one yarn which is bound in warpwise, and two weft yarns of which one is bound in by two adjacent chains, with the other being bound in by three adjacent chains.

The knitted fabric may also comprise S-twisted threads or Z-twisted threads with the same size and twist. The knitted fabric threads are of staple fiber or bleached cotton.

According to another feature of the invention, the knitted fabric has threads of S-twist or Z-twist yarns with, as a function of the desired lifting effect, a twist which exceeds to a greater or lesser extent the twist normally used with warp yarns.

The knitted fabric is formed of yarn having sizes Nm 30/1, Nm 34/1, Nm 40/1, Nm 50/1 and the like for single-ply yarns or Nm 30/2, Nm 34/2, Nm 40/2, Nm 50/2, Nm 70/2 and the like for double-ply yarns.

The threads of the knitted fabric can comprise cotton yarns with the following minium values for $\alpha$ (a) for Nm 30/1 $\alpha = 110$
(b) for Nm 34/1 $\alpha = 110$
(c) for Nm 40/1 $\alpha = 115$
(d) for Nm 50/1 $\alpha = 118$, etc.

or staple fiber yarns with the following minimum values for $\alpha$ (a) for Nm 30/1 $\alpha = 92$
(b) for Nm 34/1 $\alpha = 96$
(c) for Nm 40/1 $\alpha = 98$
(d) for Nm 50/1 $\alpha = 100$, etc.

or two-ply yarns with the following minimum values for $\alpha$ (a) for Nm 30/2 $\alpha = 108$
(b) for Nm 34/2 $\alpha = 108$
(c) for Nm 40/2 $\alpha = 112$
(d) for Nm 50/2 $\alpha = 114$
(e) for Nm 70/2 $\alpha = 118$, etc.

Of course, it is to be understood that, as used herein, Nm is the yarn size and $\alpha$ is the twist coefficient of the yarn. Also, it is to be understood that $\alpha$ is defined as follows:

$$\alpha = t/m \times \sqrt{Nm}$$

wherein t/m is the number of turns per meter.

The wound dressing is made in such a way that of threads L1, L2, L3, L4, thread L1 forms the basic stitch construction, while threads L2, L3, L4 forming the in-laid threads are inserted as slightly or greatly staggered wefts.

According to a further feature of the invention, the basic stitch construction may be formed with stitches such as open chain with a 2.0–0.2 or 0.2–2.0 lap, closed chain with a 2.0 or 0.2 lap, open tricot with a 0.2–4.2 lap, closed tricot with a 2.0–2.4 lap, and known types of stitches such as cloth and satin stitches and the like are used.

In order to increase the volume of pores and the cushioning effect, the side of the fabric remote from the wound is roughened.

A knitted fabric made from threads in accordance with the invention provides a wound dressing which provides not only a lifting action but also a very high absorptivity and consequently a high secretion retaining capacity. Knitted fabrics of highly twisted threads and lightly twisted monofilaments cannot have these characteristics due to their structure. As the knitted fabric has the same yarn in all its stitches and threads L1, L2, L3, L4, i.e., the size, twisting direction and twisting height leading to the controllability of the lifting action are the same, the desired high lifting action is achieved. If Z-twist or S-twist yarns are used whose twisting exceeds to a greater or lesser extent the conventional yarn twists (warp twists=medium twisting), there is a tendency to effect a greater or lesser raising from the wound.

The invention also relates to a wound dressing characterized by a knitted fabric web with a base stitch and with inlaid threads L2, L3, L4 inserted as greatly staggered wefts, whereby one or several of the in-laid threads L2, L3, L4 are very highly twisted and run at right angles to the warp direction.

In addition, the knitted fabric web has basic stitches L1 formed as open chain stitches with a 2.0-0.2 or 0.2-2.0 lap, closed chain stitches with a 2.0 or 0.2 lap, open tricot stitches with a 0.2-4.2 lap, or closed tricot stitches with a 2.0-2.4 lap. Furthermore, the knitted fabric web can be provided with stitches L1, e.g., of size Nm 40/1, threads L2 of size Nm 40/1 and threads L3 of size Nm 34/2 or 40/2 in the form of crepe threads or spun crepe threads of size Nm 34/1 as highly twisted monofilaments of size Nm 40/1 or Nm 34/1.

The invention is described in exeplified manner hereinafter with reference to the drawings, described as follows:

FIGS. 1 to 6 illustrate warp knitting fabric constructions made with four guide bars.

Figure 1:
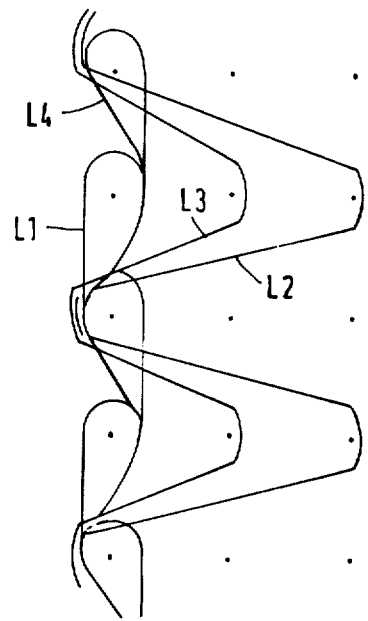
FIG. 1 is a point diagram of one embodiment of the knitted fabric.
Figure 3:
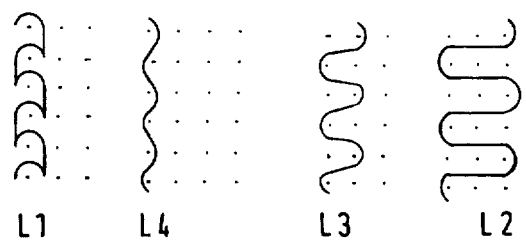
FIG. 3 illustrates in point diagrams the lapping of each thread of the fabric of FIG. 1.
Figure 4:
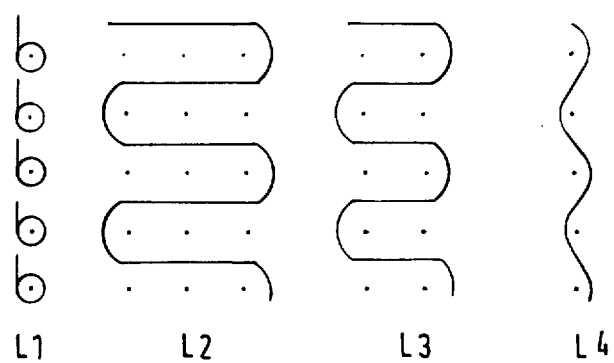
FIG. 4 illustrates in a point diagram another embodiment of the invention.
Figure 5:
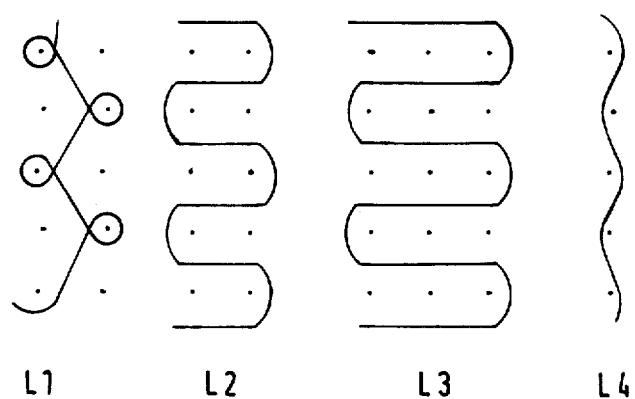
FIG. 5 illustrates in point diagram a further embodiment of the invention.
Figure 6:
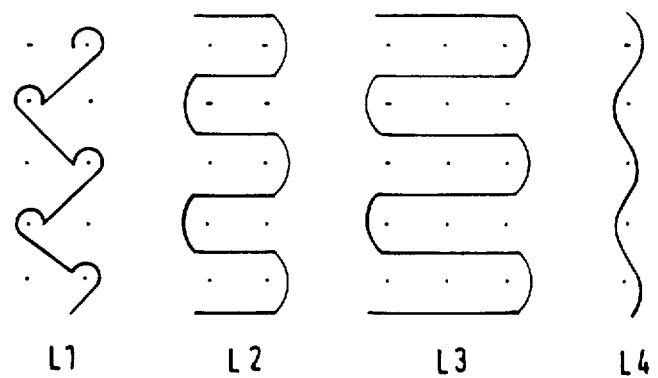
FIG. 6 illustrates in point diagram a still further embodiment of the invention.
Figure 7:
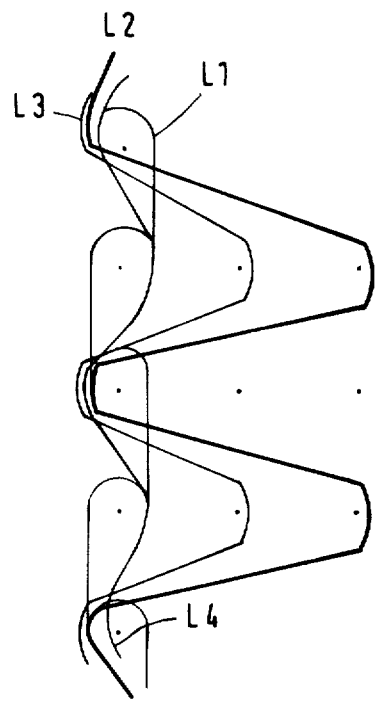
FIG. 7 is a point diagram of an additional embodiment of the invention.
Figure 9:
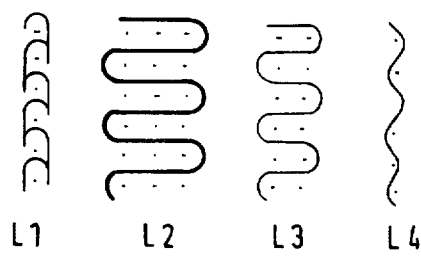
FIG. 9 illustrates in point diagram the lapping of each thread of the fabric of FIG. 7.

In each of the embodiments shown in the drawings, all the basic stitches are identified as L1 and the in-laid yarns or threads are identified as L2, L3, L4. All the yarns have the same dimensions, twisting direction and twisting height. Preferably Z-twist yarns are used which have a twist which exceeds the normal or conventional yarn twists for warp yarns. It is also possible to use S-twist yarns. The knitted fabric can also have S- or Z-twisted threads with the same dimensions and twist. The design is such that the yarns L1 may form a chain stitch, with the yarns comprising the in-laid threads L2, L3, L4 being formed as slightly or greatly staggered wefts in the knitted fabric. Teh following stitch types can be used as the basic stitch construction:

L1
 open chain 2.0-0.2 or 0.2-2.0 lap (FIGS. 1-3)
 closed chain 2.0 or 0.2 lap (FIG. 4)
 closed tricot 0.2-4.2 lap (FIG. 5)
 open tricot 2.0-2.4 lap (FIG. 6).

The in-laid threads L2, L3, and L4 can have the following weft variations:

L2
 0.0-4.4
 0.0-6.6
L3
 0.0-4.4
 0.0-6.6
L4
 0.0-2.2
 0.0-4.4
 0.0-6.6

In order to increase the volume of the pores and the cushioning action, the knitted fabric is roughened on the side remote from the wound.

The yarns for stitches and threads L1, L2, L3, L4 have the same thickness, the same warp twist and the same size, which can be, e.g., Nm 30/1, Nm 34/1, Nm 40/1 or can be heavier or lighter, as a function of the weight per square meter. It is also possible to use twisted threads Nm 30/2, Nm 34/2, Nm 40/2, Nm 50/2, Nm 60/2, etc. which can have both a Z- and an S-twist. The fibrous material can be staple fiber, bleached cotton or a mixture of staple fiber and cotton.

The knitted fabric threads can be cotton yarns with the following minimum values for $\alpha$ (a) for Nm 30/1 $\alpha = 110$
(b) for Nm 34/1 $\alpha = 110$
(c) for Nm 40/1 $\alpha = 115$
(d) for Nm 50/1 $\alpha 118$, etc.

If the knitted fabric threads comprise staple fiber yarns, the following minimum values for $\alpha$ apply (a) for Nm 30/1 $\alpha = 92$
(b) for Nm 34/1 $\alpha = 96$
(c) for Nm 40/1 $\alpha = 98$
(d) for Nm 50/1 $\alpha = 100$, etc.

The knitted fabric may also comprise double ply yarns with the following minimum values for $\alpha$ (a) for Nm 30/2 $\alpha = 108$
(b) for Nm 34/2 $\alpha = 108$
(c) for Nm 40/2 $\alpha = 112$
(d) for Nm 50/2 $\alpha = 114$
(e) for Nm 70/2 $\alpha = 118$, etc.

However, it is also possible to drop below the given minimum values.

FIGS. 7 to 12 relate to a further embodiment of the invention.

Figure 8:
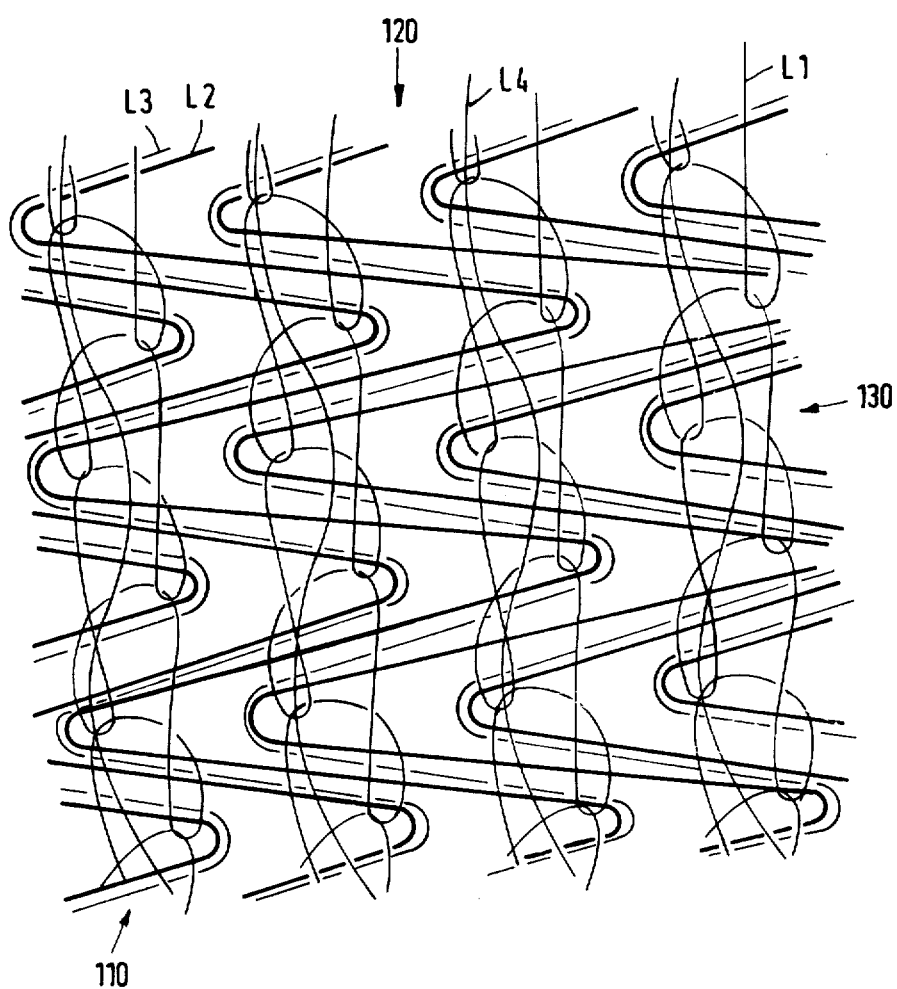
FIG. 8 is a stitch diagram of the fabric of FIG. 7.
Figure 10:
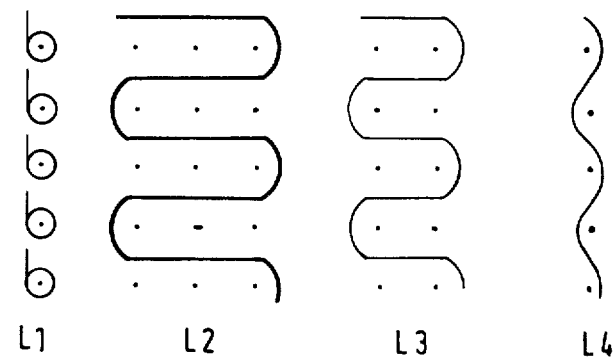
FIG. 10 illustrates in point diagram another embodiment of the invention.

In the loop structure 110 in FIG. 8, 120 indicates the warp direction and 130 the weft direction. The base stitch is formed by yarn L1, while in-laid threads L2, L3, L4 are inserted in greatly staggered wefts. Yarn L2 is thick, highly twisted and runs at right angles to the warp direction 120.

Figure 11:
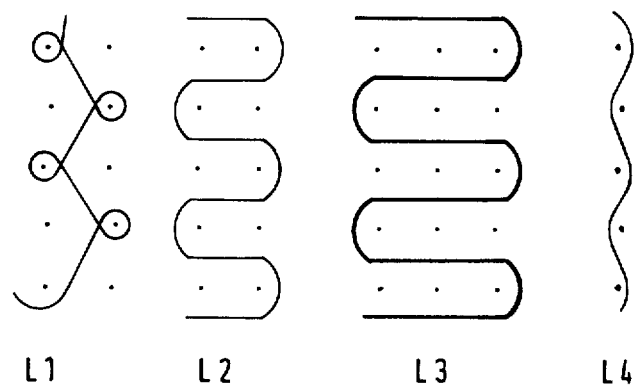
FIG. 11 illustrates in point diagram a further embodiment of the invention.
Figure 12:
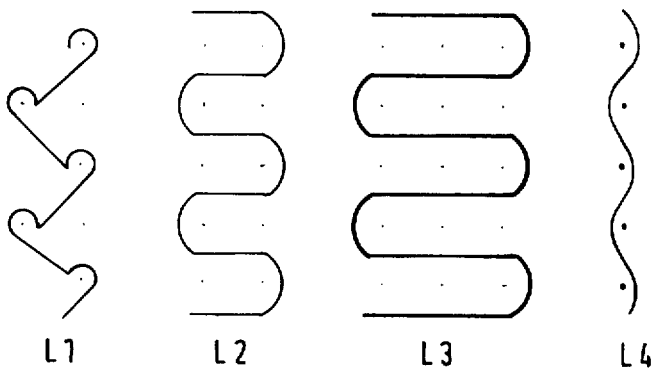
FIG. 12 illustrates in point diagram still another embodiment of the invention.

The following stitch types can be used as the base stitch construction L1:

(a) open chain 2.0-0.2 or 0.2-2.0 lap (FIGS. 7-9)
(b) closed chain 2.0 or 0.2 lap (FIG. 10)
(c) open tricot 0.2-4.2 lap (FIG. 12)
(d) closed tricot 2.0-2.4 lap (FIG. 11).

The in-laid threads L2, L3, and L4 can have the following weft variations:
L2
 0.0-4.4
 0.0-6.6
L3
 0.0-4.4
 0.0-6.6 whereby the threads L2 and L3 can be varied as follows:
L2 0.0-4.4
L3 0.0-4.4

L2 0.0–4.4
L3 0.0–6.6
L2 0.0–6.6
L3 0.0–6.6
L2 0.0–6.6
L3 0.0–4.4

L4 can be displaced via one or more needles.

Numerous other lap patterns and variations are possible for threads L2 and L3 if, e.g., lapping is carried out by using several needles. The following arrangements of the different stitches and threads are possible in the laps:

Yarn L1 of size Nm 40/1
Yarn L2 of size Nm 40/1
Yarn L3 of size Nm 34/2
   Crepe or spun twisted yarn Nm 34/1 (one highly twisted thick monofilament)
Yarn L4 of size Nm 40/1 or

Yarn L1 of size Nm 40/1
yarn L2 of size Nm 34/2 or
   Spun crepe yarn of Nm 34/1 (one highly twisted thick monofilament)
Yarn L4 of size Nm 40/1.

As a function of the weight per square meter, yarns of size Nm 40/1 can be replaced by those of Nm 34/1 and yarns of size Nm 34/1 can be replaced by crepe yarns of size Nm 40/2. Yarns of size Nm 34/2 can also be replaced by spun crepe yarns used as highly twisted monofilaments of size Nm 20/1. Depending on the desired weight per square meter it is also possible to use yarns with other dimensions in the case of similar lapping and corresponding twisting.

Yarn L4 can be inserted as a thicker voluminous yarn, which is very useful for treating the wound. Depending on the arrangement of the crepe twisted yarn, yarn L4 can be displaced to a greater or lesser extent by yarns L2 or L3.

Following the roughening process of the thread, an advantageous cushioning effect is obtained.

Monofilaments can also be replaced by other yarn dimensions. Thus, it is possible to use thick and very voluminous single yarns, which facilitate the formation of a cushion (raised cushion) and increase the absorptivity (volume of pores).

Figure 2:
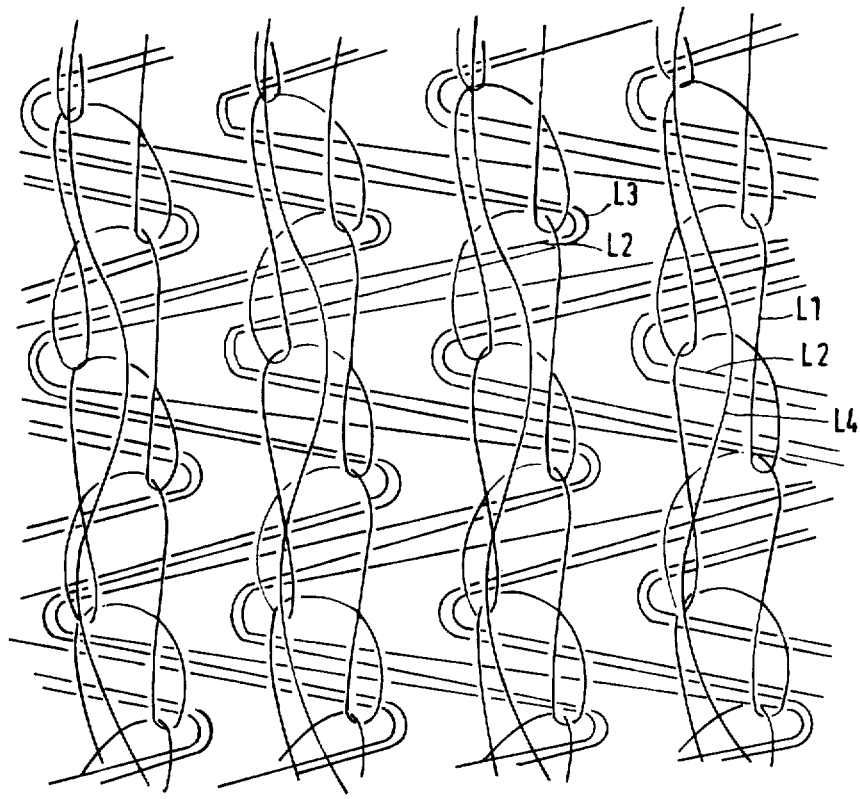
FIG. 2 is a stitch loop diagram of the fabric of FIG. 1.

It will be noted from the drawings, and particularly from FIG. 2, that the in-laid threads L2, L3, L4 comprise a yarn L4 which is bound in warpwise, and yarns L2, L3 which comprise weft yarns, of which one, L3, is bound in by two adjacent chains, with the other, L2, being bound in by three adjacent chains.

While specific embodiments of the invention have been shown and described in detail to illustrate the application of the inventive principles, it will be understood that the invention may be embodied otherwise without departing from such principles.

We claim:

1. A warp knitted fabric for use as a surgical bandage and dressing comprising four yarns arranged in a plurality of wales and causes including a first yarn comprising a basic stitch consturction (L1) and second, third, and fourth yarns bound in as in-laid threads (L2, L3, L4), said fourth yarn consisting of a thick, roughened binding yarn of high volume bound in warpwise, said second and third yarns consisting of cross filling long looped, highly twisted yarns of sinuous configuration having a twist of one of the Z-twisting direction and S-twisting direction, one of said second and third yarns being bound in between two adjacent wales and the other of said second and third yarns being bound in between three adjacent wales, said fourth yarn having the lap variation:

0.0–2.2.

2. A warp knitted fabric for use as a surgical bandage and dressing comprising four yarns arranged in a plurality of wales and causes including a first yarn comprising a basic stitch construction (L1) and second, third, and fourth yarns bound in as in-laid threads (L2, L3, L4), said fourth yarn consisting of a thick, roughened binding yarn of high volume bound in warpwise, said second and third yarns consisting of cross filling long looped, highly twisted yarns of sinuous configuration having a twist of one of the Z-twisting direction and S-twisting direction, one of said second and third yarns being bound in between two adjacent wales and the other of said second and third yarns being bound in between three adjacent wales, said yarns having said one of said S- and Z-twist of the knitted fabric having the same size and the same twist.

3. A warp knitted fabric for use as a surgical bandage and dressing comprising four yarns arranged in a plurality of wales and causes including a first yarn comprising a basic stitch construction (L1) and second, third, and fourth yarns bound in as in-laid threads (L2, L3, L4), said fourth yarn consisting of a thick, roughened binding yarn of high volume bound in warpwise, said second and third yarns consisting of cross filling long looped, highly twisted yarns of sinuous configuration having a twist of one of the Z-twisting direction and S-twisting direction, one of said second and third yarns being bound in between two adjacent wales and the other of said second and third yarns being bound in between three adjacent wales, said yarns comprising cotton yarns wherein the yarns having a yarn size of one of Nm 30/1 and Nm 34/1 have a minimum twist coefficient of 110, yarns having a yarn size of Nm 40/1 have a minimum twist coefficient of 115, and yarns having a yarn size of Nm 50/1 have a minimum twist coefficient of 118.

4. A warp knitted fabric for use as a surgical bandage and dressing comprising four yarns arranged in a plurality of wales and causes including a first yarn comprising a basic stitch construction (L1) and second, third, and fourth yarns bound in as in-laid threads (L2, L3, L4), said fourth yarn consisting of a thick, roughened binding yarn of high volume bound in warpwise, said second and third yarns consisting of cross filling long looped, highly twisted yarns of sinuous configuration having a twist of one of the Z-twisting direction and S-twisting direction, one of said second and third yarns being bound in between two adjacent wales and the other of said second and third yarns being bound in between three adjacent wales, said yarns comprising staple fiber yarns wherein yarns having a yarn size of Nm 30/1 have a minimum twist coefficient of 92, yarns having a yarn size of Nm 34/1 have a minimum twist coefficient of 96, yarns having a yarn size of Nm 40/1 have a minimum twist coefficient of 98, and yarns having a yarn size of of Nm 50/1 have a minimum twist coefficient of 100.

5. A warp knitted fabric for use as a surgical bandage and dressing comprising four yarns arranged in a plurality of wales and causes including a first yarn comprising a basic stitch construction (L1) and second, third, and fourth yarns bound in as in-laid threads (L2, L3, L4), said fourth yarn consisting of a thick, roughened binding yarn of high volume bound in warpwise, said second and third yarns consisting of cross filling long looped, highly twisted yarns of sinuous configuration having a twist of one of the Z-twisting direction and S-twisting direction, one of said second and third yarns being bound in between two adjacent wales and the other of said second and third yarns being bound in between three adjacent wales, said yarns comprising double ply yarns wherein yarns having a yarn size of Nm 30/2 and Nm 34/2 have a minimum twist coefficient of 108, yarns having a yarn size of Nm 40/2 have a minimum twist coefficient of 112, yarns having a yarn size of Nm 50/2 have a minimum twist coefficient of 114, and yarns having a yarn size of Nm 70/2 have a minimum twist coefficient of 118.

* * * * *